US009879229B2

(12) United States Patent
Shen et al.

(10) Patent No.: US 9,879,229 B2
(45) Date of Patent: Jan. 30, 2018

(54) METHOD OF VIRAL PRODUCTION IN CELLS

(75) Inventors: Chun Fang Shen, Quebec (CA); Amine Kamen, Montreal (CA)

(73) Assignee: National Research Council of Canada, Ottawa (CA)

(*) Notice: Subject to any disclaimer, the term of this patent is extended or adjusted under 35 U.S.C. 154(b) by 233 days.

(21) Appl. No.: 14/004,501

(22) PCT Filed: Feb. 15, 2012

(86) PCT No.: PCT/CA2012/000139
§ 371 (c)(1), (2), (4) Date: Sep. 11, 2013

(87) PCT Pub. No.: WO2012/122625
PCT Pub. Date: Sep. 20, 2012

(65) Prior Publication Data
US 2014/0004568 A1 Jan. 2, 2014

Related U.S. Application Data

(60) Provisional application No. 61/452,368, filed on Mar. 14, 2011.

(51) Int. Cl.
*C12N 7/00* (2006.01)

(52) U.S. Cl.
CPC ............ *C12N 7/00* (2013.01); *C12N 2500/00* (2013.01); *C12N 2500/02* (2013.01); *C12N 2710/10051* (2013.01); *C12N 2710/14051* (2013.01); *C12N 2720/12051* (2013.01)

(58) Field of Classification Search
CPC ...... A61K 45/06; A61K 2300/00; A61K 9/08; A61K 2039/515; A61K 39/12; A61K 49/0097; A61K 49/1896; C12N 7/00; C12N 15/67; C12N 2500/90; C12N 2500/00; C12N 2500/02
See application file for complete search history.

(56) References Cited

U.S. PATENT DOCUMENTS

| | | |
|---|---|---|
| 3,418,210 A | 12/1968 | Sanders et al. |
| 3,871,954 A | 3/1975 | Zuckerman |
| 3,985,615 A | 10/1976 | Kubo |
| 4,112,068 A | 9/1978 | Cabasso |
| 4,164,566 A | 8/1979 | Provost et al. |
| 4,203,801 A | 5/1980 | Telling et al. |
| 4,301,249 A | 11/1981 | Markus et al. |
| 4,721,675 A | 1/1988 | Chan et al. |
| 4,724,206 A | 2/1988 | Rupp et al. |
| 4,783,407 A | 11/1988 | Provost et al. |
| 4,783,411 A | 11/1988 | Gabliks |
| 5,021,348 A | 6/1991 | Giesa et al. |
| 5,151,359 A | 9/1992 | Miyahara et al. |
| 5,156,964 A | 10/1992 | Inlow et al. |
| 5,183,754 A | 2/1993 | Miyahara et al. |
| 5,268,292 A | 12/1993 | Robertson et al. |
| 5,360,736 A | 11/1994 | Provost et al. |
| 5,506,129 A | 4/1996 | Sangar |
| 5,514,376 A | 5/1996 | Giesa et al. |
| 5,705,364 A | 1/1998 | Etcheverry et al. |
| 5,721,121 A | 2/1998 | Etcheverry et al. |
| 5,766,603 A | 6/1998 | Giesa et al. |
| 5,824,536 A | 10/1998 | Webster et al. |
| 5,856,179 A | 1/1999 | Chen et al. |
| 5,989,878 A | 11/1999 | Kim et al. |
| 6,001,616 A | 12/1999 | Kim et al. |
| 6,162,636 A | 12/2000 | Kim et al. |
| 6,180,401 B1 | 1/2001 | Chen et al. |
| 6,210,922 B1 * | 4/2001 | Cote et al. ............... 435/69.1 |
| 6,238,891 B1 | 5/2001 | Maiorella et al. |
| 6,267,967 B1 | 7/2001 | Johnston et al. |
| 6,566,118 B1 | 5/2003 | Atkinson et al. |
| 6,630,343 B1 | 10/2003 | Bartenschlager |
| 6,995,006 B2 | 2/2006 | Atkinson et al. |
| 7,344,873 B2 | 3/2008 | Xie et al. |
| 2002/0119530 A1 | 8/2002 | Maiorella et al. |
| 2003/0190710 A1 | 10/2003 | deVries et al. |
| 2003/0224502 A1 | 12/2003 | Johnston et al. |
| 2004/0048368 A1 | 3/2004 | Chen et al. |
| 2004/0214289 A1 | 10/2004 | deVries et al. |
| 2004/0259205 A1 | 12/2004 | Etcheverry et al. |

(Continued)

FOREIGN PATENT DOCUMENTS

| | | |
|---|---|---|
| AU | 780112 | 5/2002 |
| JP | 19960351427 | 7/1998 |

(Continued)

OTHER PUBLICATIONS

Ben-Israel H, Kleinberger T. Adenovirus and cell cycle control. Front Biosci. May 1, 2002;7:d1369-95.*
Johnston RE, Faulkner P. Reversible inhibition of Sindbis virus penetration in hypertonic medium. J Virol. Jan. 1978;25(1):436-8.*
Song B, Liu JJ, Yeh KC, Knipe DM. Herpes simplex virus infection blocks events in the G1 phase of the cell cycle. Virology. Feb. 15, 2000;267(2):326-34.*
Koseki I. [Influence of a hypertonic medium on cell susceptibility to foot-and-mouth disease virus]. Arq Inst Biol (Sao Paulo). Oct.-Dec. 1978;45(4):273-80.*
Shapiro GS, Van Peursem C, Ornelles DA, Schaack J, DeGregori J. Recombinant adenoviral vectors can induce expression of p73 via the E4-orf6/7 protein. J Virol. Jun. 2006;80(11):5349-60.*

(Continued)

*Primary Examiner* — Rachel B Gill
(74) *Attorney, Agent, or Firm* — Cermak Nakajima & McGowan LLP; Shelly Gust Cermak

(57) ABSTRACT

A method of using a cell to produce virus is provided involving growing cells under hyperosmotic conditions during a growth phase of the cells, infecting or transfecting the cells grown under hyperosmotic conditions with a virus, and maintaining the infected or transfected cells under less stressful conditions during a production phase of the infected or transfected cells to produce more of the virus. Viral productivity is improved by this method.

15 Claims, 6 Drawing Sheets

(56) References Cited

U.S. PATENT DOCUMENTS

| | | | |
|---|---|---|---|
| 2005/0118698 | A1 | 6/2005 | Vorlop et al. |
| 2005/0221393 | A1 | 10/2005 | Maiorella et al. |
| 2005/0272029 | A1 | 12/2005 | Saunier et al. |
| 2005/0272124 | A1 | 12/2005 | Chen et al. |
| 2006/0035364 | A1* | 2/2006 | Wright et al. ............... 435/239 |
| 2006/0141509 | A1 | 6/2006 | Johnston et al. |
| 2007/0117131 | A1 | 5/2007 | Groner |
| 2007/0184529 | A1 | 8/2007 | Etcheverry et al. |
| 2008/0206812 | A1 | 8/2008 | Atkinson et al. |
| 2008/0305546 | A1 | 12/2008 | Bauer et al. |
| 2009/0042273 | A1 | 2/2009 | Johnston et al. |
| 2010/0035342 | A1 | 2/2010 | Cheng et al. |
| 2010/0035343 | A1 | 2/2010 | Cheng et al. |
| 2010/0055754 | A1 | 3/2010 | Pitera et al. |
| 2010/0068698 | A1 | 3/2010 | McCown et al. |
| 2010/0184147 | A1 | 7/2010 | Cheng et al. |
| 2011/0097785 | A1 | 4/2011 | Warthen et al. |
| 2011/0269233 | A1* | 11/2011 | Malphettes et al. .......... 435/440 |

FOREIGN PATENT DOCUMENTS

| | | |
|---|---|---|
| KR | 20000040714 | 7/2000 |
| KR | 20090123622 | 12/2009 |
| WO | WO0014205 | 3/2000 |
| WO | WO02076578 | 10/2002 |
| WO | WO2006109781 | 10/2006 |

OTHER PUBLICATIONS

Sobsey MD, Meschke JS. Virus survival in the environment with special attention to survival in sewage dropletes and other environmental media of fecal or respiratory origin. WHO Virus Survival Report draft, Aug. 21, 2003. http://www.unc.edu/courses/2008spring/envr/421/001/WHO_VirusSurvivalReport_21Aug2003.pdf.*

ATCC Animal Cell Culture Guide. 2014, Accessed Jan. 6, 2016, https://www.atcc.org/~/media/PDFs/Culture%20Guides/AnimCellCulture_Guide.ashx.*

ThermoFischer Scientific. "Cell Culture Environment". 2015, accessed Jan. 6, 2016, https://www.thermofisher.com/us/en/home/references/gibco-cell-culture-basics/cell-culture-environment.html.*

Ryan JA. Corning Guide for Identifying and Correcting Common Cell Growth Problems, Corning Inc., New York, NY. Mar. 2008.*

IPRP from corresponding PCT/2012/000139 dated Sep. 17, 2013.

English Abstract of JP19960351427.

Extended European Search Report issued in respect of corresponding EP application No. 12758094.2.

Shen, Chun Fang et al., Hyperosmotic pressure on HEK 293 cells during the growth phase, but no the production phase, improves adenovirus production, Journal of Biotechnology, vol. 157, No. 1, 2011, pp. 228-236.

Nadeau, I. et al, Improvement of recombinant protein production with the human adenovirus 293S expression system using fed-batch strategies, Biotechnology and Bioengineering, 1996, vol. 51, pp. 613-623.

Zhang, J et al., Optimization of the physiochemical parameters for the culture of Bombyx mori insect cells used in recombinant protein production, Journal of Biotechnology, 1994, vol. 33, No. 3, pp. 249-258.

Warren, James C. et al., Animal cells, hybridomas, human antibody production effect of osmolality of the cellular microenvironment introduction, Encyclopedia of industrial biotechnology, 2010, pp. 1-16.

Begin, M.E. et al., Enhanced production of infectious rotavirus in BSC-1 cell cultures by various factors in the presence or absence of trypsin, Journal of General Virology, 1980, vol. 51, No. 2, pp. 263-270.

Aunins JG. (2000) Viral vaccine production in cell culture. In: Spier RE, editor. Encyclopedia of Cell Technology. vol. 2. (John Wiley & Sons) pp. 1182-1217.

Bibila TA, Flickinger MC. (1991) a structured model for monoclonal antibody synthesis in exponentially growing and stationary phase hybridoma cells. Biotechnol. Bioeng. 37:210-226.

Bishop JM, Maldano RL, Garry RF, Allen PT, Bose HR, Waite MRF. (1976) Effect of medium of lowered NaCl concentration on virus release and protein synthesis in cells infected with reticuloendotheliosis virus. J. Virol. 17:446-452.

Cherlet M, et al. (1999) Hybridoma cell behaviour in continuous culture under hyperosmotic stress. Cytotechnol. 29:71-84.

Chomczynski P, et al., (1987) Single-step method of RNA isolation by acid guanidinium thiocyanate-phenol chloroform extraction. Anal Biochem. 162:156-9.

Coroadinha AS et al., (2006) Effect of osmotic pressure on the production of retroviral vectors: enhancement in vector stability. Biotechnol. Bioeng. 94:322-329.

Ferreira TB, et al., (2005) Two different serum-free media and osmolality effect upon human 293 cell growth and adenovirus production. Biotechnol. Lett. 27:1809-1813.

Ferreira TB, et al., (2009) 293 cell cycle synchronisation in adenovirus production. Biotechnol. Prog. 25:235-243.

Freshny RI. (2005) Culture of Animal Cells: A Manual of Basic Technique, 5th ed. (Wiley-Liss.) pp. 115-143.

Kim NS, Lee GM. (2002) Response of recombinant Chinese hamster ovary cells to hyperosmotic pressure: effect of Bcl-2 overexpression. J. Biotechnol. 95:237-248.

Klyushnichenko V, et al., (2001) Improved HPLC method in the analysis of adenovirus particles. J Chromatogr B Anal Technol Biomed Life Sci. 755:27-36.

Lee MS, Lee GM. (2000) Hyperosmotic pressure enhances immunoglobulin transcription rate and secretion rates of KR12H-2 transfectoma. Biotechnol. Bioeng. 68:260-268.

Maranga L, et al., (2005) Characterization of changes in PER.C6™ cellular metabolism during growth and propagation of a replication-deficient adenovirus vector. Biotechnol. Bioeng. 90:645-655.

Oh SKW, et al., (1995) Intracellular responses of productive hybridomas subjected to high osmotic pressure. Biotechnol. Bioeng. 46:525-535.

Øyaas K, et al., (1994). Hyperosmotic hybridoma cell cultures: Increased monoclonal antibody production with addition of glycine betaine. Biotechnol. Bioeng. 44:991-998.

Ozturk SS, Palsson BO. (1991). Effect of medium osmolality on hybridoma growth, metabolism, and antibody production. Biotechnolo. Bioeng. 37:989-993.

Sharfstein S, et al., (2007) Molecular response to osmotic shock. In: Cellular Engineering: System Biology, vol. 5. Edited by Mohamed A-R, Martin F. (Springer publisher).

Shen CF, et al., (2010) Reassessing culture media and critical metabolites that affect adenovirus production. Biotechnol. Prog. 26:200-207.

Sun Z, et al. (2004) Hyperosmotic stress in murine hybridoma cells: effects on antibody transcription, translation, post-translation processing and the cell cycle. Biotechnol. Prog. 20:576-589.

Transfiguracion J, et al., (2008) Rapid and reliable quantification of reovirus type 3 by high performance liquid chromatography during manufacturing of Reolysin. J Pharm Biomed Anal. 48, 598-605.

Transfiguracion J, et al., (2011) Development and validation of a HPLC method for the quantification of baculovirus particles. J Chromatogr B Analyt Technol Biomed Life Sci. 879, 61-68.

Waite MRF, et al., (1970) Inhibition of sindbis virus production by media of low ionic strength: intracellular events and requirements for reversal. J. Virol. 5:60-71.

Zhang C, et al., (2006) The importance of 293 cell cycle phase on adenovirus vector production. Enzy. Microb. Technol. 39:1328-1332.

ISR/WO from corresponding PCT/2012/000139 dated May 9, 2012.

English Abstract of KR 20000040714.

English Abstract of KR 20090123622.

English Abstract of WO2006109781.

(56) References Cited

OTHER PUBLICATIONS

Olejnik, A et al., Effect of hyperosmolarity on recombinant protein productivity in baculovirus expression system, Journal of Biotechnology, May 2003, vol. 102, No. 3, pp. 291-3000.

* cited by examiner

METHOD OF VIRAL PRODUCTION IN CELLS

CROSS-REFERENCE TO RELATED APPLICATIONS

This application is a national stage filing under 35 U.S.C. § 371 of International Patent PCT/CA2012/000139 filed Feb. 15, 2012, which claims the benefit under 35 U.S.C. § 119(e) of U.S. Provisional Application Ser. No. 61/452,368 filed Mar. 14, 2011, disclosure of each of which is incorporated by reference herein in its entirety.

FIELD OF THE INVENTION

The present invention is related to a method of producing viruses in cells.

BACKGROUND OF THE INVENTION

Animal cell cultures may be used as cellular factories for the production of bioproducts. Significant efforts have been dedicated to the development and optimization of animal cell-culture conditions to increase the titer of the final product. In the case of specific antibodies, improving specific antibody productivity in mammalian cell cultures may be achieved with hyperosmotic stress, which can be easily induced by the addition of salts or sugars to a culture medium (Sharfstein 2007). The effect of hyperosmotic stress in increasing specific antibody production has been observed in many hybridoma cell lines and in Chinese hamster ovary (CHO) cells (Ozturk 1991; Oh 1995; Ryu 2000; Kim 2002). The majority of the studies on hyperosmotic stress in mammalian cell cultures observed an approximately two-fold increase in specific antibody productivity; however, the increase in specific productivity was not accompanied by an increase in overall yield because the maximum viable cell density was significantly decreased at higher osmolalities. In a study of the function of glycine betaine as an osmoprotectant, it was demonstrated that glycine betaine can alleviate the growth repression observed in osmotically stressed cultures and can thereby improve antibody production (Øyaas 1994). Several reports concluded that metabolism, cell growth, cell density, product secretion, and specific antibody productivity in mammalian cells are strongly affected by osmotic conditions (Ozturk 1991; Kim 2002).

Viral production in cell systems is the result of two consecutive phases: the growth phase and the virus production phase. Production yield is not only determined by cell physiological state in the virus production phase, but also by the history of the cells as a consequence of cell culture environment during the growth phase. Determination of optimal conditions that maximize viral production yield is not obvious. Thus, in contrast to the effect of hyperosmotic pressure on specific antibody production, specific adenovirus productivity in HEK 293 cells was inhibited when both the cell growth and virus production phases were carried out in hyperosmotic media (Ferreira 2005) or when the cells were grown in isotonic media and the virus was produced in hyperosmotic media (Shen 2010) (note: the osmolality of isotonic media is 290 mOsm; the osmolality of most commercial media is near isotonic). Also, the volumetric productivity of retroviruses was generally lower at elevated osmolality, although the stability of retroviral vectors was enhanced under hyperosmotic conditions (Coroadinha 2006). The effect of osmotic stress on adenovirus production has not been extensively studied, and its utilization to improve viral production yields has not been reported.

There remains a need in the art to develop new methods for producing viral vectors in cells that can result in improved viral production yields.

SUMMARY OF THE INVENTION

Surprisingly, it has now been found that growing cells under hyperosmotic conditions during the growth phase followed by maintaining the cells under osmotic conditions during the production phase that are less stressful than the growth phase markedly improves viral production yield.

Thus, in one aspect of the present invention, there is provided a method of using a cell to produce virus comprising: growing cells under hyperosmotic conditions during a growth phase of the cells; infecting or transfecting the cells grown under hyperosmotic conditions with a virus; and, maintaining the infected or transfected cells under less stressful osmotic conditions during a production phase of the infected or transfected cells to produce more of the virus.

The present method is suitable for production of any kind of virus. Some examples of viruses are non-budding and budding viruses. Non-budding viruses include, for example, adenovirus, adeno-associated virus and reovirus. Budding viruses include, for example, retrovirus, lentivirus and baculovirus. The present method is especially suited for non-budding viruses, more especially adenoviruses. As viral production in cellular systems is commercially often geared toward producing viral vectors, the present method is particularly useful for production of viral vectors. Viral vector particles produced by the method are useful for transfecting other cells with nucleic acid molecules of interest for the production of proteins of interest.

Any cells that are suitable for producing viruses may be used in the present method. Such cells are preferably eukaryotic cells, for example mammalian or insect cells. Some specific examples of cells include human embryonic kidney 293 (HEK 293) cells, A549 cells, Chinese hamster ovary (CHO) cells, Hela cells and SF9 insect cells.

Viral production in cell systems results from two consecutive phases: a growth phase and a production phase. The growth phase involves culturing cells under conditions to maximize the number and size of the cells. In order to increase osmolality during the growth phase, salts (e.g. NaCl, KCl, $KNO_3$), sugars (e.g. sucrose, glucose, fructose) or other chemicals are typically added to the cultured cells. For hyperosmotic conditions, an osmolality of about 330 mOsm or greater is desirable, provided the osmolality is not so high as to induce cell death. Osmolalities of about 340 mOsm or greater, or about 370 mOsm or greater, without inducing cell death are useful. Osmolalities in a range of from about 330 mOsm to about 420 mOsm or about 330 mOsm to about 370 mOsm or about 370 mOsm to about 420 mOsm are noteworthy. Osmolalities as high as about 500 mOsm may be achieved without inducing cell death, and with proper conditioning, the cells may be able to survive osmolalities as high as about 700 mOsm or even about 900 mOsm.

Once the growth phase is complete, the cells may be infected or transfected with the virus. Infection or transfection with the virus induces the cells to produce more of the virus, thus the cells enter into the production phase. Infection or transfection may be accomplished by any suitable method, a number of which are well known in the art (Aunins 2000). Infected or transfected cells are then maintained under less stressful osmotic conditions during the production phase. Less stressful osmotic conditions typically comprise an osmolality in a range of about 250 mOsm to about 325 mOsm, more particularly from about 280 mOsm to about 300 mOsm, yet more particularly about 285 mOsm to about 295 mOsm, for example about 290 mOsm.

Cells are typically cultured on a cell culture medium containing necessary nutrients for cell survival. Such media are generally well known in the art (Feshney 2005). Achievement of hyperosmotic conditions during the growth phase can be accomplished by adding salts, sugars or other chemicals as described above to the culture medium. Achievement of less stressful osmotic conditions for the production phase may be accomplished through complete medium replacement or through culture dilution before viral infection.

Viral production yield is advantageously increased by the method of the present invention. The yield may be increased by about 1.5 times or more. An increase of about 2 times or more or even 3 times or more is possible. An increase in yield of over 11 times has been observed. An increase in yield of about 2-4 times is typical. After the production phase, viral particles produced may be recovered by means generally known in the art. The general process of viral production is known in the art (Aunins 2000).

Osmolarity is a measure of the osmoles of solute per liter of solution. A capital letter M is used to abbreviate units of mol/L. Since the volume of solution changes with the amount of solute added as well as with changes in temperature and pressure, osmolarity is difficult to determine. Osmolality is a measure of the moles (or osmoles) of solute per kilogram of solvent expressed as (mol/kg, molal, or m). Since the amount of solvent will remain constant regardless of changes in temperature and pressure, osmolality is easier to evaluate and is more commonly used, and often preferred, in practical osmometry. Most commercially available osmometers report results using osmolality units mOsm/kg. It will be understood by one skilled in the art that the present invention may be expressed in terms of osmolarity rather than osmolality.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
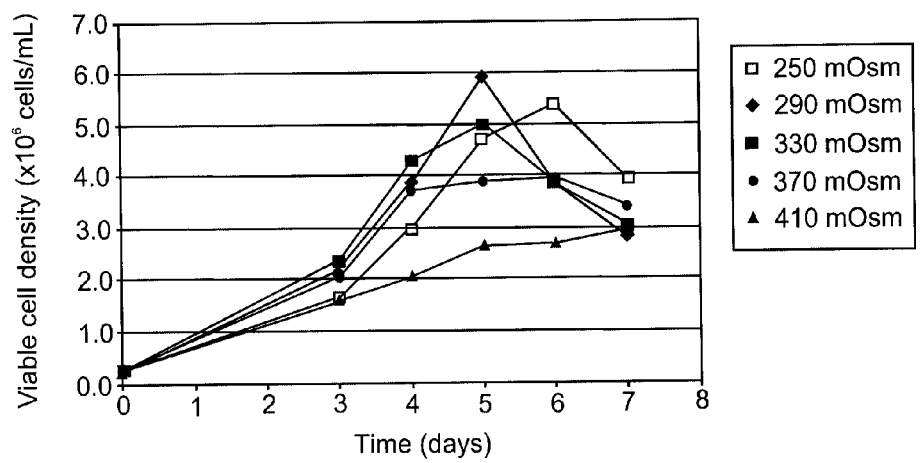
FIG. 1 is a graph depicting effect of media osmolality on the growth of HEK 293 SF cells in media with different osmolalities (□, 250 mOsm; ♦, 290 mOsm; ■, 330 mOsm; ●, 370 mOsm; ▲, 410 mOsm).

The singular and combined effects of osmolality on the phases of cell growth and virus production were evaluated in culture media with osmolalities ranging from 250 to 410 mOsm. A two-factor, five-level full factorial design was used to investigate the effect of osmotic stress on cell physiology, as determined through the characterization of cell growth, cell metabolism, cell viability, cell cycle, cell RNA and total protein content, and virus productivity. Overall, the results show that the growth of cells under hyperosmotic conditions induced favorable physiological states for viral production, and the specific virus productivity was improved by more than 11-fold when the medium's osmolality was increased from 250 to 410 mOsm during the cell growth phase. Both hypo- and hyperosmotic stress in the virus production phase reduced virus productivity by as much as a factor of six. Optimal virus productivity was achieved by growing cells in media with an osmolality of 370 mOsm or greater, followed by a virus production phase at an osmolality of about 290 mOsm. Compared to standard growth and production conditions in isotonic media, the shift from high to low osmolality between the two phases resulted in a two- to three-fold increase in virus yields. This hyperosmotic pressure effect on virus productivity was reproduced in five different commercial serum-free media.

The behavior of mammalian cells, such as hybridoma cell lines and CHO-derived clones, in response to osmotic stress has been investigated in many studies in an effort to understand the impact of hyperosmotic stress on cell growth, viability, cell metabolism, and antibody production (Sharfstein 2007). In contrast, the response of HEK 293 cells to osmotic stress in the context of virus production had not been studied in detail and required further examination to better understand the effect of osmotic stress on the cell behavior during the cell growth phase. It has now been found that changes in the cells' physiological state during the growth phase have an impact on the cells' viral productivity. In fact, not only do the cells respond to their environment, but the maintenance of the cells also has a profound effect on the overall performance of the cells during the production phase.

A notable decrease in the specific growth rate and a reduction in the maximum viable cell density of HEK 293 cells under hyperosmotic conditions suggest that the mechanisms by which osmotic stress suppresses cell growth are likely to be similar to those observed in other cell lines. The reduced maximum viable cell density in the cultures with hyperosmotic media might be (or partially) attributed to increased cell volume (meaning greater biomass), as the consumption rates of amino acids in the cultures using media with osmolalities of 290 mOsm or greater do not exhibit significant differences.

In contrast to most reported studies in which medium with a single osmolality was used for both cell growth and antibody- or virus-production phases, this invention involved independent evaluation of the effects of various osmolalities during the cell growth phase and during the virus production phase. It was found that the physiological state of the cells (such as growth rate, cell diameter, RNA content, and protein content) changed after the cells were exposed to osmotic stress during the cell growth phase. These changes, depending on whether they were hyper- or hypoosmotic stresses, either stimulated or inhibited the specific virus productivity. However, osmotic stress over the production phase inhibited virus productivity. A factorial design of experiments permitted decoupling of the interactions between the osmotic effects of cell growth medium and of virus production medium on the virus productivity and to find optimal osmolalities for cell growth (330 to 370 mOsm) and virus production (290 mOsm) media to maximize the virus production yield.

Media with osmolalities of 290 mOsm or greater were often used to study osmotic stress (Ozturk 1991; Oh 1995). Some early studies observed an inhibitory effect of hypoosmotic pressure on the production of Sindbis virus and reticuloendotheliosis virus when NaCl concentrations were lowered in media used during the virus production phase (Waite 1970; Bishop 1976). The effect of hypoosmotic pressure on cell growth and virus (or antibody) production has been rarely revisited since then. Results herein demonstrate that, in addition to a decreased specific cell-growth rate, virus production was also inhibited by the use of hypoosmotic media during the virus production phase. More importantly, specific virus production and cell viability at 42 hpi were always lower in the infected cultures using cells grown in the hypoosmotic medium (250 mOsm), indicating these cells were in a less favorable physiological state for viral production. Therefore, cell growth and virus production could be significantly impaired if hypoosmotic media are used in viral manufacturing processes.

Significant efforts have been dedicated to understanding the effect of hyperosmotic stress on cellular pathways, such as protein processing and the cell cycle, and to finding correlations between antibody production and cellular responses (Sharfstein 2007). The sole impact of the growth medium's osmotic stress, as reflected by the changes in cellular physiological state, on virus production can be assessed when there is no or minimal limitation on the cells' viral productivity due to other factors during the virus production phase. To this end, the virus productivity in the cultures using an optimal production medium (290 mOsm) was used to evaluate the effect of osmotic stress in the growth medium.

Increased RNA content (30% to 40% more) in osmotically stressed cells has been reported by other groups (Oh 1995; Lee 2000) when osmolality was increased by 50 and 100 mOsm, respectively. Sun et al. (Sun 2004) found that the total RNA content was similar in stressed and control cells in mid-exponential phase but became significantly higher than in control cells during stationary phase. However, the content of total cellular RNA or proteins in the cells grown in the media with osmolalities of 330 mOsm or greater was not higher than in cells grown at 290 mOsm in the present invention. With regard to the relative change in RNA and protein content, the relative change in virus productivity was one order of magnitude higher than that of either RNA or total protein content. This result might indicate that the physiological state of cells grown in hyperosmotic media was more favorable for one or more steps of the adenovirus replication cycle during the virus production phase. This favorable physiological state, however, was not really reflected by parameters such as cell size, content of total RNA and protein, and distribution of cell-cycle status measured in the experiments.

Improvement in adenovirus production due to changes in the cells' physiological state has been reported before. Xie and Goochee (Xie 2008) obtained a two- to three-fold enhancement in adenovirus productivity when the culture temperature was switched to a sub-optimal setting (33° C.) during part or all of cell growth phase and then raised back to physiologically optimal temperature (37° C.) during virus production. Zhang et al. (Zhang 2006) found that HEK 293 cells in S phase of the cell cycle may produce more adenovirus. Therefore, Ferreira et al. (Ferreira 2009) employed various strategies to increase the proportion of the cell population in S phase to improve virus production.

Increasing the osmolality of cell growth medium dramatically improved the cell viability at 42 hpi in the infected cultures, which may improve the cells' ability to perform the packaging step of the adenovirus replication cycle, thus improving the virus yield. However, the cell viability was also high in some cultures, but their virus production was low when hyperosmotic media were used in the virus production phase. It has now been found that maintaining a good "cell physiological state," (e.g., growing cells in hyperosmotic media and improving cell viability) are only prerequisites for improving virus productivity. Other environmental conditions also play crucial roles during the virus production process.

The increased glucose consumption and lactate production rates in infected cultures using cells grown in hyperosmotic medium were due to the increased cell volume (or biomass), as mentioned before. This result supports previous observations regarding hybridoma cell lines exposed to hyperosmotic media (Ozturk 1991). In addition, the accumulated lactate and ammonia concentrations were in the range of 11 to 23 mM and 1.6 to 2.4 mM, respectively, which are within the ranges observed in standard mammalian cell cultures and are unlikely to be the main factors causing the significant differences observed in virus productivity (Shen 2010).

The osmolality of cultures in both cell growth and virus production phases significantly affects the final virus productivity, but in different ways. The virus productivity can be improved by two- to three-fold through optimization of the stimulatory effect of hyperosmotic pressure during the cell growth phase and elimination of the inhibitory effect of osmotic stress during virus production phase. The improvement of virus productivity can be achieved through complete medium replacement or through culture dilution before viral infection.

Materials and Methods:

Cell Lines, Media, and Virus

Serum-free HEK 293SF cells were adapted from HEK 293S to a Hybridoma-SFM (Invitrogen Corp., Grand Island, N.Y.). The Hybridoma-SFM (LC-SFM) was custom-made with a low calcium concentration and without sodium chloride to allow flexibility in the preparation of concentrated medium while maintaining a low osmolality. A basal medium, which comprised 25% 2× LC-SFM, 50% CD293 (Invitrogen Corp., Grand Island, N.Y.), 0.1% BSA, and 25% NaCl solution at various osmolalities, was prepared to have a respective osmolality of 250, 290, 330, 370, and 410 mOsm. Cells were maintained at 25 mL culture in 125 mL plastic shake flasks (Corning, N.Y.) at 37° C. and 5% $CO_2$ in a humidified incubator. Cells were sub-cultured to densities of $2\times10^5$ and $2.5\times10^5$ cell/mL three times a week. Other culture media, including Pro293S-CDM (Lonza, Walkersville, Md.), SFM4transfx-293 (Hyclone, Logan, Utah), and NSFM13 (Shen 2010), were also used to investigate adenovirus production.

The adenovirus used for infection was a type 5 adenovirus containing the green fluorescent protein (GFP) under the control of the CMV promoter. The titer of the virus was $1.7\times10^{10}$ IVP/mL, and aliquots were stored at −80° C.

Batch Culture

HEK 293SF cells were adapted to the basal medium at osmolalities of 250, 290, 330, 370, and 410 mOsm for at least three passages before being used for further studies. The batch culture was inoculated at a density of $0.25\times10^6$ cells/mL and was sampled regularly for cell count and the analysis of metabolites and residual nutrient concentrations.

Infected Culture

HEK 293SF cells grown to a density of about $1\times10^6$ cells/mL in the various media were centrifuged at 300×g for 5 min. The cells were then re-suspended in fresh media with the same or a different osmolality to a cell density of $1\times10^6$ cells/mL, and the cells were infected with adenovirus at a multiplicity of infection of 10 infectious particles per cell (an MOI of 10 IVP/cell was used throughout the study). Some cultures were grown to $2\times10^6$ cells/mL and then diluted with fresh media to a density of $1\times10^6$ cells/mL before the viral infection. The infected culture was sampled at 42 hpi for subsequent analysis.

Design of Experiments for Studying Adenovirus Production

HEK 293SF cells were grown in the basal media with five different osmolalities for at least three passages, centrifuged at 300×g for 5 min, and re-suspended in fresh production media at various osmolalities according to a two-factor (osmolality of cell growth media and osmolality of virus production media), five-level (five different osmolalities) full factorial design ($5^2$), as shown in Table 1.

TABLE 1

| | | Osmolality of media used for cell growth (mOsm) | | | | |
|---|---|---|---|---|---|---|
| | | 250 | 290 | 330 | 370 | 410 |
| Osmolality of virus production media (mOsm) | 250 | + | + | + | + | + |
| | 290 | + | + | + | + | + |
| | 330 | + | + | + | + | + |
| | 370 | + | + | + | + | + |
| | 410 | + | + | + | + | + |

Statistical Analysis of Experimental Data

The trend of the osmotic effect of cell growth media and virus production media (factors) on virus productivity, cell viability, and metabolism (responses) was statistically analyzed (DOE++ software, ReliaSoft Corporation, Tucson, Ariz.) and presented in term-effect plots. The term effect of cell growth media on the responses is reported as the mean of five samples prepared using production media with five different osmolalities (five levels) but with identical cells grown under separate osmolalities. The term effect of virus production media is calculated using the same principle.

Analytical Methods

Total cell count, viability, diameter, and compactness were determined by Cedex™ (Roche Innovatis AG, Bielefeld, Germany), an automated cell-counting system based on the Trypan Blue exclusion method for determining cell viability. Total cell count and viability of infected cultures were determined by hemacytometer counts (Hausser Scientific, Horshaw, Pa.) using the erythrosin B dye exclusion method. Glucose, lactate, and ammonia were measured with a Vitros™ DT60 II Chemistry System (Ortho-Clinical Diagnostic, Inc., Rochester, N.Y.). Amino acids were measured by HPLC using the Waters AccQ.Tag™ method. Total virus-particle titers were assayed by HPLC (Klyushnichenko (2000). Medium osmolality was measured using an Advanced™ Micro Osmometer (Advanced Instruments, Inc., Norwood, Mass.).

Total cellular RNA was isolated according to a known protocol (Chomczynski 1987) using TRIZOL™ reagent. Briefly, 5 mL of culture at a density of about $1\times10^6$ cells/mL was centrifuged, and the cell pellet was lysed with 1 mL of TRIZOL™ reagent. The concentration of isolated RNA was quantified using a NanoDrop™ 1000 Spectrophotometer (Thermo Fisher Scientific, Wilmington, Del.). Total protein was estimated according to a known procedure (Sun 2004).

Cell-cycle analysis was performed according to a known the procedure (Cherlet 1999). Briefly, cells were grown to a density of about $1\times10^6$ cells/mL in media with various osmolalities for at least three passages. The cells were harvested, washed with PBS, fixed with 70% ethanol, and stained with propidium iodide before being analyzed using a BD™ LSR II flow cytometer (BD Biosciences, San Jose, Calif.).

Example 1: Effect of Osmotic Stress on Cell Growth, Viability, and Diameter

A medium comprising 50% LC-SFM, 50% CD293, and 0.1% BSA was used as a basal medium in this experiment, as this medium was able to support both substantial cell growth and excellent virus production (Shen 2010). The cell growth in the medium with 330 mOsm was comparable to that observed with 290 mOsm, and it doubled after 24 hours. However, the specific cell growth rate (μ) in both hypo- (250 mOsm) and hyperosmotic media (370 and 410 mOsm) was observed to gradually decrease and then stabilize after two to three passages. The specific cell growth rate of cultures in media with osmolalities of 250 or 370 mOsm was about 80% of that observed in the culture with an osmolality of 290 mOsm in maintenance cultures. Increasing the medium osmolality to 410 mOsm reduced the specific cell growth rate to 60% of that observed in normal cultures.

Figure 2:
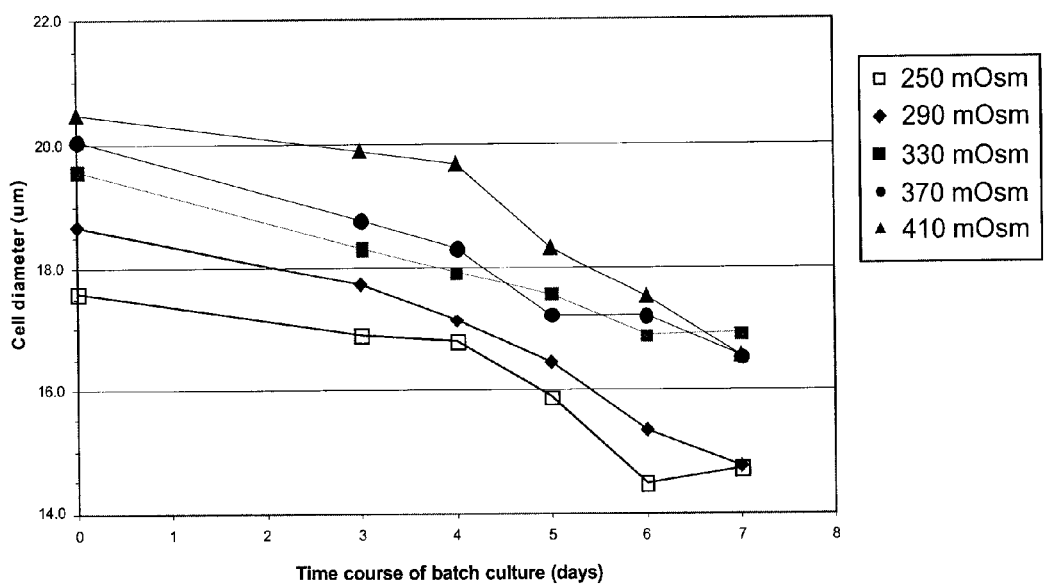
FIG. 2 is a graph depicting effect of media osmolality on cell diameter during the phase of cell growth (□, 250 mOsm; ♦, 290 mOsm; ■, 330 mOsm; ●, 370 mOsm; ▲, 410 mOsm)

The maximum viable cell density decreased in the batch cultures with both hypo- and hyperosmotic media and declined significantly with increasing medium osmolality (FIG. 1). Analysis of the residual concentration of amino acids revealed that the rates of amino acid consumption in the cultures using media with osmolalities of 290 mOsm or greater were similar, whereas the consumption rate was slightly lower in the cultures with a medium osmolality of 250 mOsm. The cell diameter (or volume) increased significantly after being cultured in the media with increasing osmolality, especially when the medium's osmolality was increased from 250 to 330 mOsm (FIG. 2, day 0). The diameter of cells in all cultures decreased gradually over the time course of batch culture.

Example 2: Effect of Medium Osmolality on Adenovirus Production

Figure 3:
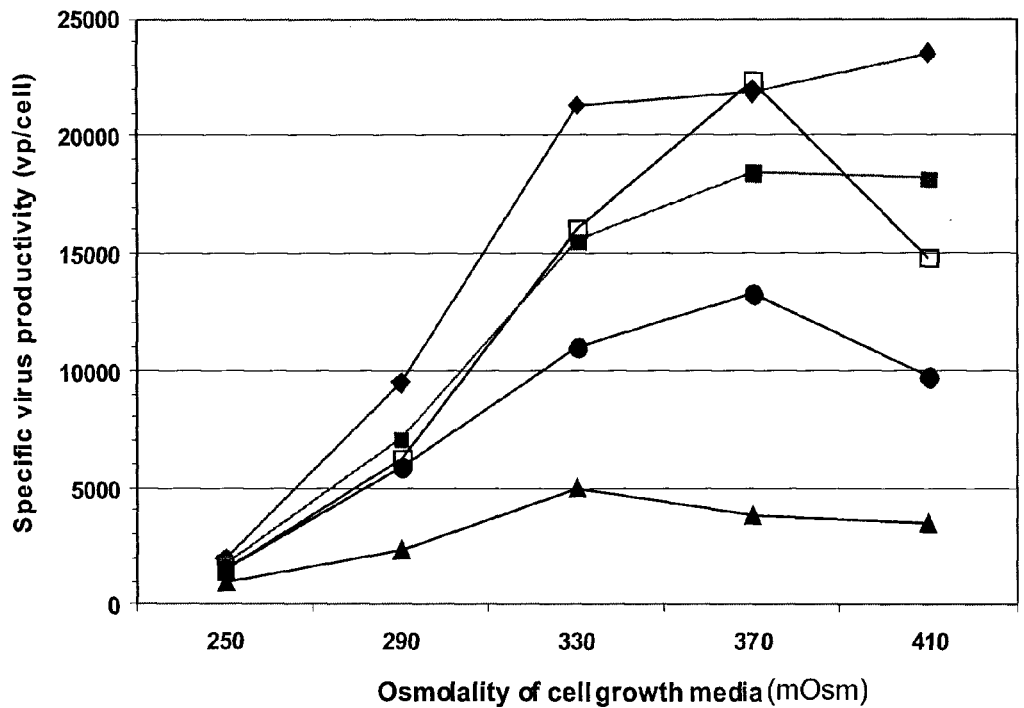
FIG. 3 is a graph depicting osmotic effect of cell growth and virus production media on the specific virus productivity (osmolality of production medium: □, 250 mOsm; ♦, 290 mOsm; ■, 330 mOsm; ●, 370 mOsm; ▲, 410 mOsm).

To gain insight into the effect of osmotic stress on virus production, a two-factor, five-level full factorial design was employed to investigate the impact of osmotic stress on the cellular physiological state during the cell growth phase and its effect on cell metabolism and virus productivity during the virus production phase. As shown in FIG. 3, the specific productivity of adenovirus increased almost linearly when the osmolality of medium used for cell growth was increased from 250 to 330 mOsm, although the extent of the productivity increase was dependent on the osmolality of media used for virus production. Additional improvement in the virus yield was limited when the osmolality of cell growth media was increased beyond 330 mOsm. In the best-case scenario, where the osmolality of the virus production medium was 290 mOsm, the difference of virus yield between the cultures using cells grown at 250 and 410 mOsm was 11.7-fold (2016 vp/cell vs. 23507 vp/cell). This result indicates that the maintenance of cells during the culture process had a pronounced effect on the specific production of virus.

Figure 4:
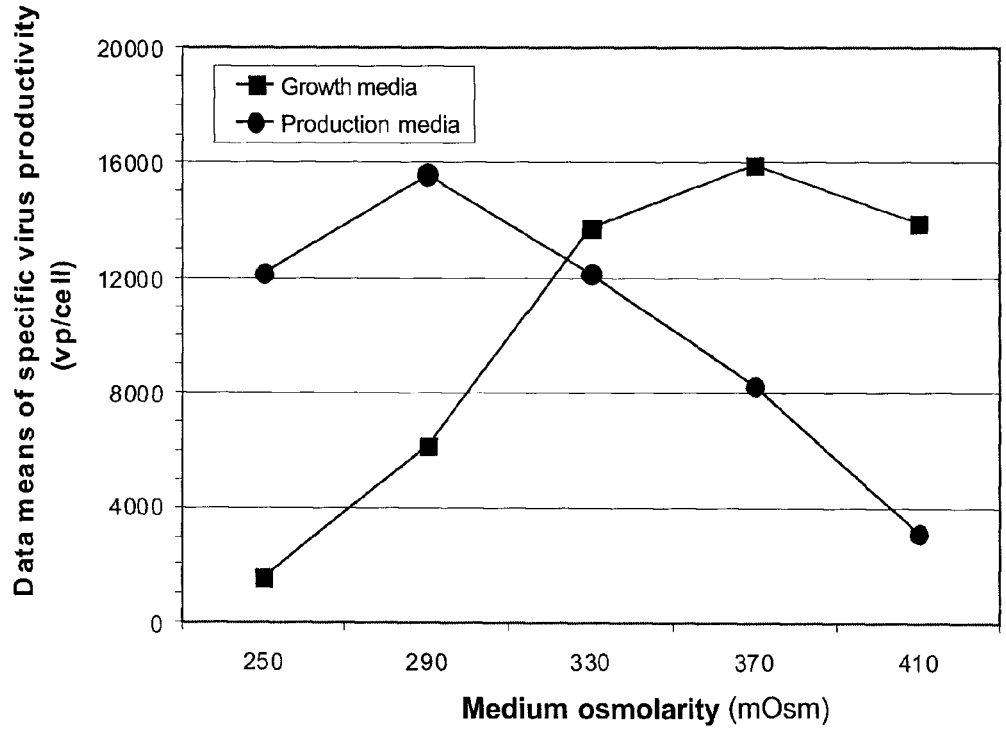
FIG. 4 is a graph depicting term effect of medium osmolality used for cell growth and virus production on the specific virus production (■, term effect of growth medium; ●, term effect of production medium).

The osmotic effect of media used for cell growth and virus production in this set of experiments was statistically analyzed. The term effect as shown in FIG. 4 indicated that the virus production was higher in the cultures using the cells grown in media over a relatively broad osmolality range of between 330 to 410 mOsm, whereas the optimal osmolality of production medium was in a narrower range centered at about 290 mOsm. As FIG. 4 shows, isotonic medium (290 mOsm) was optimal for virus production, as both hypo- and hyperosmotic media caused reduced or severely suppressed virus production. The virus yield was reduced by 6.7-fold when the osmolality of the virus production medium was increased from 290 mOsm to 410 mOsm.

Statistical analysis also revealed that the trend of increasing osmotic effect of the cell growth medium on virus productivity was almost opposite to that of the virus production media. There was no overlap in the optimal range of osmolality between the two media; therefore, optimal virus production cannot be achieved if one medium with the same osmolality is used for both cell growth and virus production. This may explain why a decline instead of an increase in virus production was observed when a medium with high osmolality was used for both cell growth and virus production (Ferreira 2005).

Example 3: Influence of the Cellular Physiological State on Virus Productivity

Cell diameter, RNA content, total protein content, and the distribution of cells within the cell cycle were examined in cultures grown under various medium osmolalities before the cells were re-suspended in fresh media for virus production. As described in the previous section, the cell diameter (or volume) increased significantly after being cultured in media with increased osmolality. A significant correlation was found between the specific virus productivity (measured in vp/cell) and the diameter of cells used for virus production, especially for cells grown at 290 mOsm ($R^2$=0.98) and 330 mOsm ($R^2$=0.96). A further analysis of specific virus productivity, on the basis of per-cell volume (measured in vp/$\mu m^3$), revealed a similar pattern, which indicated that increasing cell size played only a minor role in the increase in specific virus productivity. The cells grown in media with osmolalities greater than 330 mOsm were generally more productive on the basis of per-cell volume.

Figure 5:
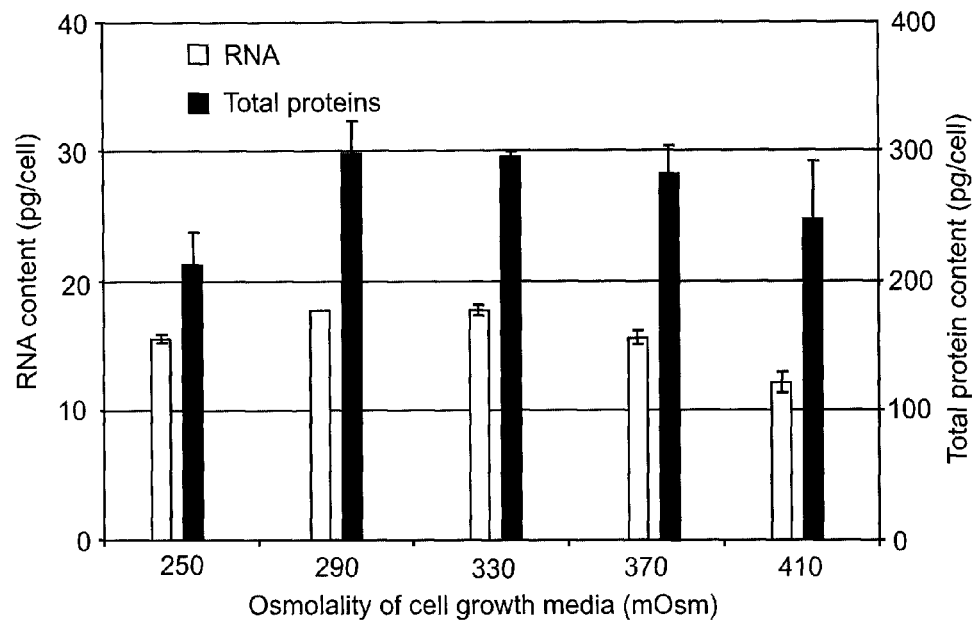
FIG. 5 is a graph depicting osmotic effect of cell growth media on total content of cellular RNA and protein.

Referring to FIG. 5, total cellular RNA content increased by 13% when the osmolality of cell-growth medium was increased from 250 to 290 mOsm. However, the RNA content declined significantly when the medium's osmolality was further increased from 330 to 410 mOsm. The effect of the osmolality of cell growth medium on total cellular protein content was similar to that observed on RNA content. No significant correlation was found between specific virus productivity and the content of total cellular RNA or proteins. Instead, the RNA content was significantly correlated with the specific cell growth rate ($R^2$=0.97). Cell-cycle analysis by a flow cytometry revealed that there was no significant difference in the relative fractions of the cell population that were in G1, S, and G2 phases, caused by the growth of cells in medium with osmolalities ranging from 250 to 370 mOsm. The distribution of cells in the cell cycle varied from about 43% in G1 phase and 15% in G2 phase to 36% in G1 phase and 23% in G2 phase when the medium osmolality was increased to 410 mOsm.

Figure 6:
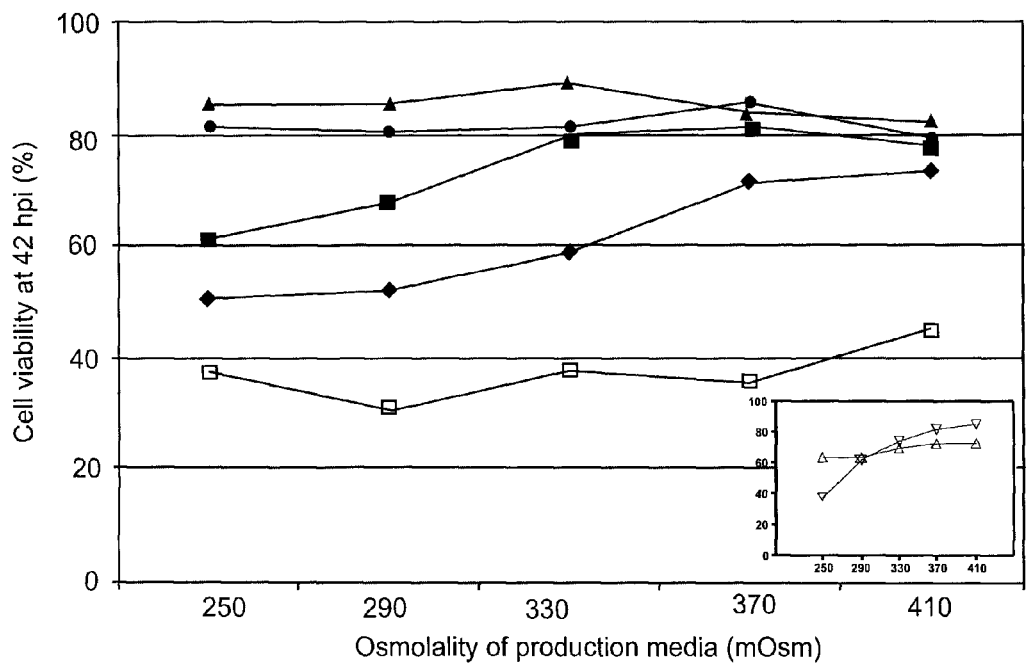
FIG. 6 is a graph depicting osmotic effect of media used for cell growth and virus production on the cell viability at 42 hpi. Cells grown in media with different osmolalities (□, 250 mOsm; ♦, 290 mOsm; ■, 330 mOsm; ●, 370 mOsm; ▲, 410 mOsm). The insert shows the term effect of the osmolarity of cell growth media (∇) and virus production media (Δ) on the cell viability at 42 hpi.

Example 4: Analysis of Cell Viability and Metabolism During the Virus Production Phase and its Effect on Virus Productivity Cell viability measured at 42 hpi during virus production phase significantly improved with increasing osmolality of the media used during the cell growth phase (FIG. 6). Increasing the osmolality of virus production medium from 250 to 370 mOsm also moderately improved cell viability at 42 hpi in cultures using cells grown with medium osmolalities of 290 and 330 mOsm, respectively. A clearer trend of the osmotic effect of the media used for cell growth and virus production on cell viability at 42 hpi was demonstrated by an analysis of cell viabilities in the infected cultures, and shown by the term effect (FIG. 6, insert).

Some correlations between cell viability and specific virus productivity were observed among each group of five cultures for which the same medium was used for virus production. The $R^2$ values were 0.76, 0.95, 0.97, 0.86, and 0.69 for the five groups of cultures with production-medium osmolalities of 250, 290, 330, 370, and 410 mOsm, respectively. However, when attempting to correlate cell viability and specific virus production for all 25 cultures, a much lower value ($R^2$=0.38) was obtained.

Figure 7:
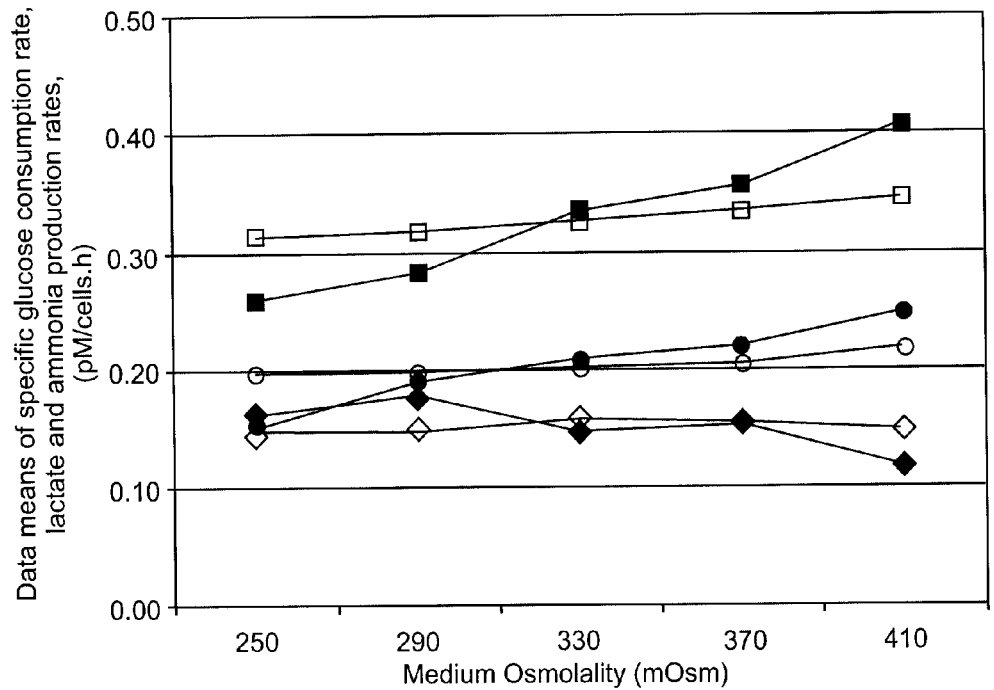
FIG. 7 is a graph depicting term effects of the osmolality of cell growth medium (cgm) and virus production medium (vpm) on the specific glucose consumption rate (●-$q_{glu\text{-}cgm}$, ○-$q_{glu\text{-}vpm}$), lactate production rate (■-$q_{lac\text{-}cgm}$, □-$q_{lac\text{-}vpm}$), and ammonia production rate (♦-$q_{NH\text{-}cgm}$, ◇-$q_{NH3\text{-}vpm}$) during the phase of virus production.

The rate of glucose consumption and the rates of lactate and ammonia production were measured for each specific culture during the virus production process. The term effects of the osmolalities of cell growth and virus production media on the specific rates of glucose consumption ($q_{glu}$) and lactate and ammonia production ($q_{lac}$ & $q_{NH3}$) are presented in FIG. 7. The $q_{glu}$ increased in a statistically significant manner with respect to the increasing osmolality of medium used for cell growth. Hyperosmotic pressure of the virus production media also slightly increased the glucose uptake rate for the cultures where the cells were grown in high-osmolality media. The residual glucose concentration in all of the cultures remained within a range of 6.7 to 14.4 mM. No significant correlation ($R^2=0.38$) was found between the $q_{glu}$ and the specific virus production rate for the 25 cultures or sub-groups of five samples.

Similarly to what was observed for the $q_{glu}$, the $q_{lac}$ increased with the increasing osmolality of media used for cell growth. The accumulated lactate concentration in the cultures at 42 hpi was in the range of 11 to 23 mM.

Statistically, the $q_{NH3}$ was not significantly affected by the osmolality of virus production media. Cells grown in media with high osmolality, especially at 410 mOsm, produced less ammonia. The accumulated ammonia concentration in the individual culture at 42 hpi was in the range of 1.6 to 2.4 mM. No significant correlation was found between the $q_{NH3}$ and the level of virus production.

The effect of the osmolality of cell growth medium was further examined to gain insight into the role of increased cell size on the cellular metabolism during the virus production phase. The $q_{glu}$, $q_{lac}$, and $q_{NH3}$ in the cultures using cells grown in the media with different osmolalities were recalculated on the basis of per-cell volume. The results indicated that the $q_{glu}$ was 55, 58, 55, 57, and 62 attomolar/ ($\mu m^3$ cell volume·h) (note: 1 aM=$10^{-15}$ mM); $q_{lac}$ was 93, 86, 88, 93, and 101 aM/($\mu m^3$ cell volume·h); and $q_{NH3}$ was 58, 54, 39, 40, and 30 aM/($\mu m^3$ cell volume·h) for the cultures grown in the medium with respective osmolalities of 250, 290, 330, 370, and 410 mOsm. This result indicates that there was no dramatic difference in $q_{glu}$ and $q_{lac}$ in the cultures using cells grown in the media with different osmolalities. The increased $q_{glu}$ or $q_{lac}$ on a per-cell basis (FIG. 7) was mainly due to increased cell size. In contrast to the $q_{glu}$ or $q_{lac}$, the $q_{NH3}$ decreased significantly in the cells grown in media with increasing osmolality, decreasing by almost 50% less in the culture using cell grown in medium with an osmolality of 410 mOsm. Again, these results indicate that the maintenance of cells grown in media with various osmolalities has a profound effect on the $q_{NH3}$.

Figure 8:
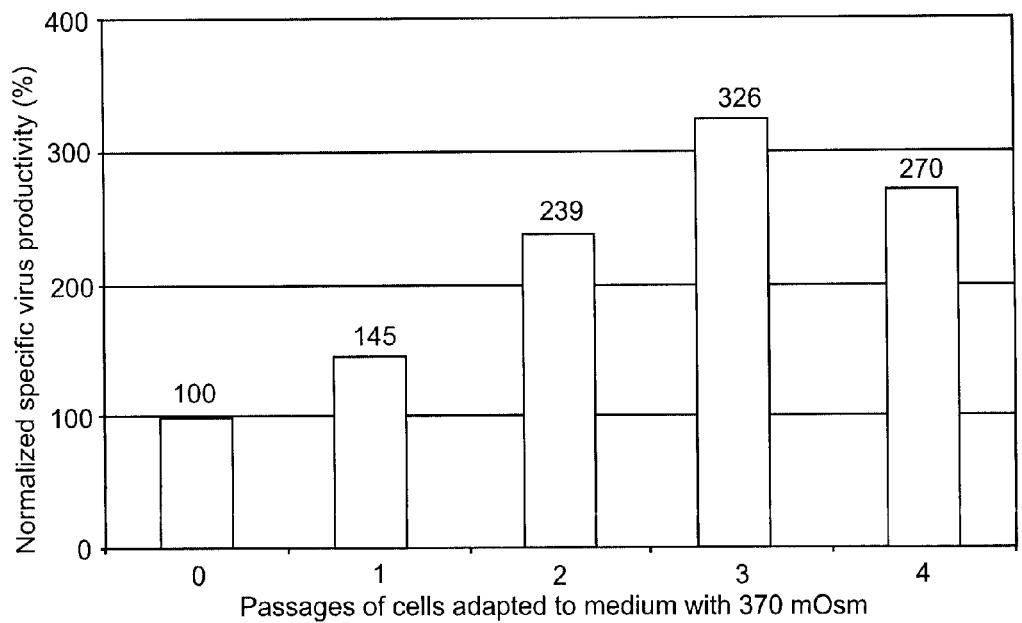
FIG. 8 is a graph depicting Influence of cell passages on the effect of hyperosmotic stress on the virus productivity.

Example 5: Influence of the Cell Passage Number in Hyperosmotic Medium on Virus Productivity HEK 293 cells were grown in a hyperosmotic medium at an osmolality of 370 mOsm for various periods of time to identify an optimal passage number (number of times of sub-culturing) for adapting the cells to high osmolality and achieving maximum virus productivity. A positive effect (45% increase) of hyperosmotic pressure on virus production was observed after one passage. An approximately 2.5-fold productivity increase was achieved after three or more passages (one week or longer) of cell growth in the hyperosmotic medium (FIG. 8).

Figure 9:
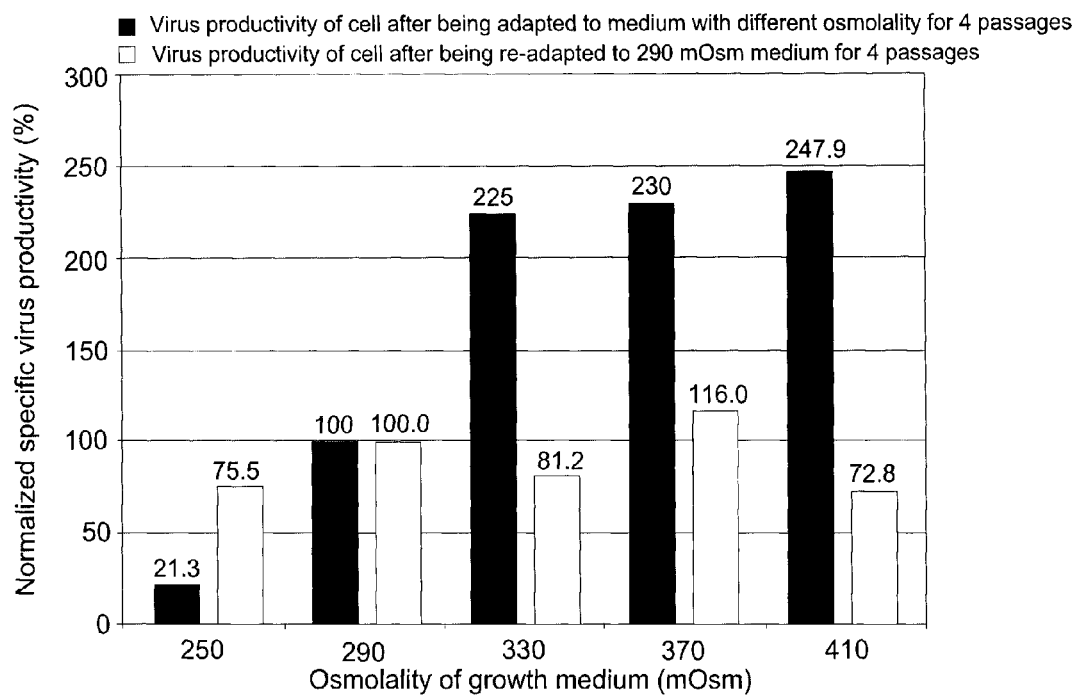
FIG. 9 is a graph depicting reversibility of the osmotic stress on the adenovirus production. (■), virus productivity of cell after being adapted to medium with different osmolality for 4 passages; (□), virus productivity of cell after being re-adapted to 290 mOsm medium for 4 passages.

The cell growth-related beneficial effect of osmotic stress on adenovirus production was also reversible. Cell populations originally adapted to the osmolalities of 250, 290, 330, 370, and 410 were de novo adapted over three passages to an osmolality of 290 mOsm medium and were tested for adenoviral production. In all cases, viral productivity returned to standard values (FIG. 9).

Example 6: Potential Industrial Application of Cell-Growth Hyperosmotic Pressure on the Improvement of Virus Production A complete medium exchange at the time of virus infection was employed in the experiments described in the previous sections. The cell growth-related stimulatory effect of hyperosmotic pressure on virus production was also examined in cultures without utilizing medium replacement, but through pre-infection dilution of the culture to adjust osmolality during the virus production phase. Two cultures with medium osmolalities of 290 and 370 mOsm were grown to a cell density of $2\times10^6$ cells/mL and were then diluted to a cell density of $1\times10^6$ cells/mL by using either the same medium or a medium with a lower osmolality (210 mOsm) before the viral infection to adjust the osmolality to the target value of 290 mOsm. A 2.3-fold increase in both specific and volumetric virus productivity was achieved in the culture using the 370 mOsm medium over the one using 290 mOsm medium for the cell growth phase. However, the volumetric productivity of both cultures was only half of that achieved in cultures using a complete medium replacement before the viral infection. This result suggests that the positive effect of hyperosmotic stress during the cell growth phase can be achieved through diluting cultures at higher cell densities before infection. This approach is simple to operate and is more easily scalable than the one requiring a medium replacement.

Figure 10:
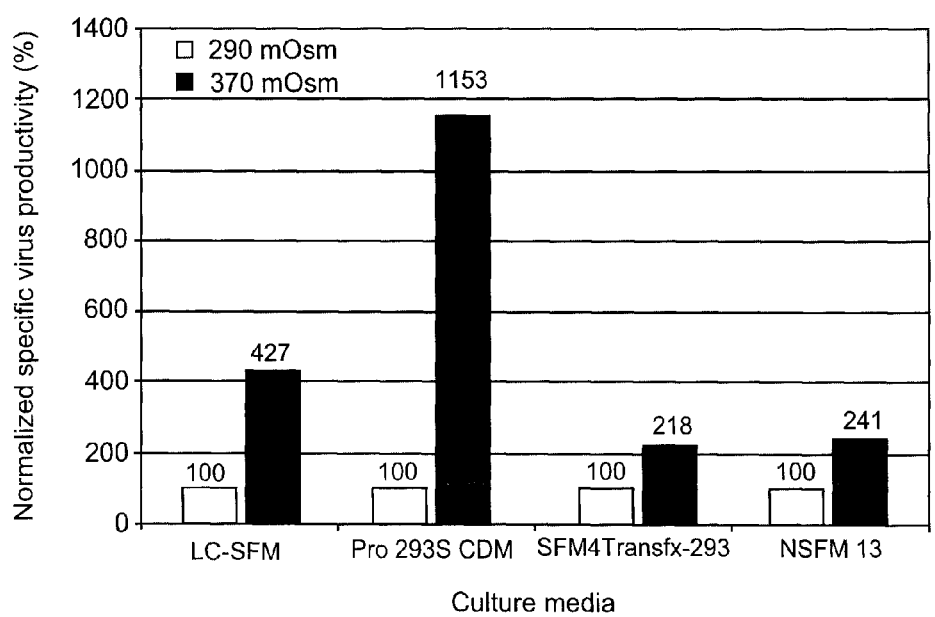
FIG. 10 is a graph depicting effect of hyperosmotic pressure on the adenovirus production in cultures using different serum free media.

To further demonstrate that the present method is generic and amenable to industrial applications, the effect of hyperosmotic pressure-induced cell growth on adenovirus production was also examined in cultures with four other different serum-free media and validated in a 20-L controlled bioreactor production. Overall, the specific virus productivity of cells grown in media at an osmolality of 370 mOsm was two- to four-fold of the one achieved with a growth medium at an osmolality of 290 mOsm (FIG. 10). The 11.5-fold increase achieved in the culture using Pro293S CDM was much higher and is an exceptional result that is probably caused by a much lower volumetric virus productivity (almost one log lower than that achieved in other media), and therefore, the stimulatory effect of hyperosmotic stress was more significant. The virus productivity at an osmolality of 290 mOsm in the 20-L bioreactor production with cells adapted at an osmolality of 370 mOsm was superior by threefold to the control culture realized in a shake flask with cells adapted at an osmolality of 290 mOsm.

Example 7: Osmotic Effect on Productivity of Reovirus by HEK 293 Cell

Figure 11:
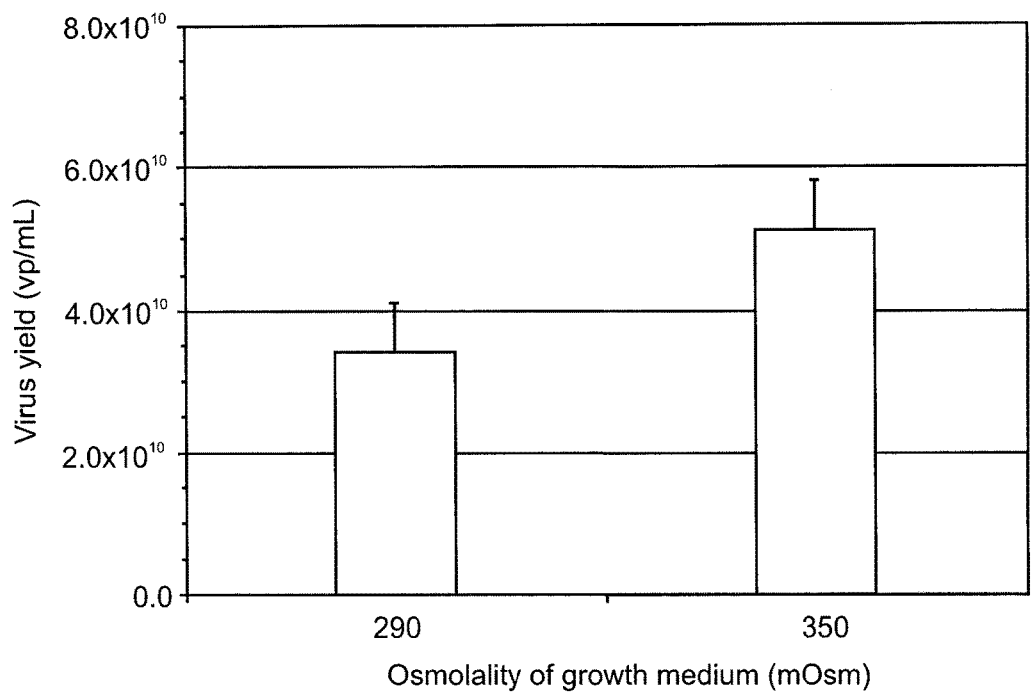
FIG. 11 is a graph depicting effect of osmolality of growth media on the productivity of reovirus by HEK 293 cell. The osmolality of production medium was 290 mOsm.

HEK 293S cells were adapted to a proprietary formulation cell culture medium (SAFC Biosciences, St Louis, Mo.) with respective osmolality of 290 and 350 mOsm at 37° C. for at least 3 passages. The cells were then grown to a density of about $1\times10^6$ cells/ml in various media, and centrifuged at 300×g for 5 min. The cell pellet was resuspended to a fresh production medium with an osmolality of 290 mOsm, and infected with a reovirus at an MOI of 0.5. The infected culture was harvested at 90 hours of post infection. Total virus particles in the harvested culture were quantified according to a HPLC method (Transfiguracion 2008). FIG. 11 shows that the virus yield in the culture using cells grown in the medium with an osmolality of 350 mOsm was 50% higher than that obtained in the culture using the cells grown in the medium with an osmolality of 290 mOsm.

Example 8: Osmotic Effect on Productivity of Baculovirus by Sf9 Insect Cell

The baculovirus was produced using *Spodoptera frugiperda* Sf9 and Sf900 II medium (Life Technologies Inc., Burlington, ON, Canada). Briefly, the Sf9 cells were adapted to Sf900 II media with respective osmolality of 290, 350 and 410 mOsm in 125 ml shake-flasks at 27° C. for at least 3 passages before being used for test of virus production. The cells were grown to a density of about $2.5 \times 10^6$ cells per ml in the various media and then centrifuged at 300×g for 5 min. The cell pellet was re-suspended to a cell density of $2.5 \times 10^6$ cells/mL in fresh media with an osmolality of 290 or 350 mOsm, and infected with a recombinant baculovirus expressing β-galactosidase at an MOI of 1. At 60 h post-infection (hpi), the virus was harvested by centrifuging the cell culture (Beckman, Model J-6B) at 3000 rpm for 10 min at 4° C. The supernatant containing baculovirus was filtered through a pre-sterilized 250 ml vacuum driven disposable 0.22 mm Stericup™ filtration system. The sterile filtrates were stored at 4° C. for subsequent analysis.

Figure 12:
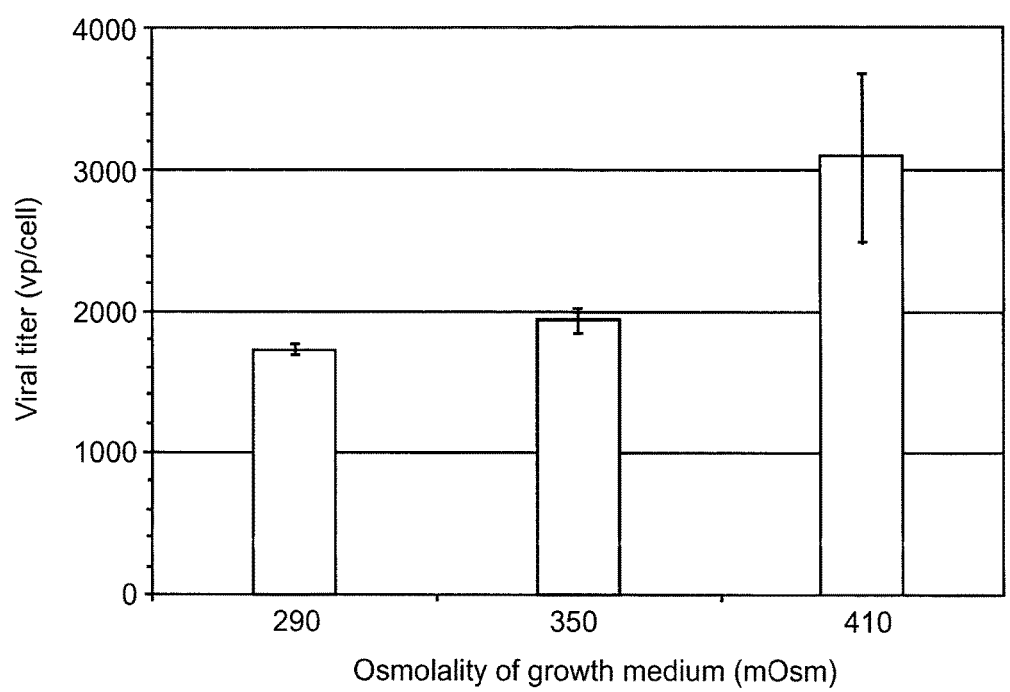
FIG. 12 is a graph depicting effect of osmolality of growth media on the productivity of baculovirus by Sf9 insect cell. The osmolality of production medium was 350 mOsm.

Concentration of total virus particles in the supernatant was quantified by a HPLC method (Transfiguracion 2011). FIG. 12 shows that specific virus productivity was significantly higher in the cultures using Sf9 cells grown in media with higher osmolality, e.g. 410 mOsm, especially when the virus production was carried out in a production medium with an osmolality of 350 mOsm. This result also indicates that the optimal osmolality of production media required for baculovirus production by insect cell could be different from that used for virus productions in mammalian cultures.

REFERENCES

The contents of the entirety of each of which are incorporated by this reference.

Aunins J G. (2000) Viral vaccine production in cell culture. In: Spier R E, editor. *Encyclopedia of Cell Technology*. Vol. 2. (John Wiley & Sons) pp. 1182-1217.

Bibila T A, Flickinger M C. (1991) A structured model for monoclonal antibody synthesis in exponentially growing and stationary phase hybridoma cells. *Biotechnol. Bioeng.* 37:210-226.

Bishop J M, Maldonado R L, Garry R F, Allen P T, Bose H R, Waite M R F. (1976) Effect of medium of lowered NaCl concentration on virus release and protein synthesis in cells infected with reticuloendotheliosis virus. *J. Virol.* 17:446-452.

Cherlet M, Marc A. (1999) Hybridoma cell behaviour in continuous culture under hyperosmotic stress. *Cytotechnol.* 29:71-84.

Chomczynski P, Sacchi N. (1987) Single-step method of RNA isolation by acid guanidinium thiocyanate-phenol-chloroform extraction. *Anal Biochem.* 162:156-9.

Coroahinha A S, Silva A C, Pires E, Coelho A, Alves P M, Carrondo M J T. (2006) Effect of osmotic pressure on the production of retroviral vectors: enhancement in vector stability. *Biotechnol. Bioeng.* 94:322-329.

Ferreira T B, Ferreira A L, Carrondo M J T, Alves P M. (2005) Two different serum-free media and osmolality effect upon human 293 cell growth and adenovirus production. *Biotechnol. Lett.* 27:1809-1813.

Ferreira T B, Perdigão R, Silva A C, Zhang C, Aunins J G, Carrondo M J T, Alves P M. (2009) 293 cell cycle synchronisation in adenovirus production. *Biotechnol. Prog.* 25:235-243.

Fresheny R I. (2005) *Culture of Animal Cells: A Manual of Basic Technique*, 5th ed. (Wiley-Liss.) pp. 115-143.

Kim N S, Lee G M. (2002) Response of recombinant Chinese hamster ovary cells to hyperosmotic pressure: effect of Bcl-2 overexpression. *J. Biotechnol.* 95:237-248.

Klyushnichenko V, Bernier A, Kamen A, Harmsen E. (200) Improved HPLC method in the analysis of adenovirus particles. *J Chromatogr B Anal Technol Biomed Life Sci.* 755:27-36.

Lee M S, Lee G M. (2000) Hyperosmotic pressure enhances immunoglobulin transcription rate and secretion rates of KR12H-2 transfectoma. *Biotechnol. Bioeng.* 68:260-268.

Maranga L, Aunins J G, Zhou W. (2005) Characterization of changes in PER.C6™ cellular metabolism during growth and propagation of a replication-deficient adenovirus vector. *Biotechnol. Bioeng.* 90:645-655.

Oh S K W, Chua F K F, Choo A B H. (1995) Intracellular responses of productive hybridomas subjected to high osmotic pressure. *Biotechnol. Bioeng.* 46:525-535.

Øyaas K, Ellingsen T E, Dyrset N, Levine D W. (1994). Hyperosmotic hybridoma cell cultures: Increased monoclonal antibody production with addition of glycine betaine. Biotechnol. Bioeng. 44:991-998.

Ozturk S S, Palsson B O. (1991). Effect of medium osmolality on hybridoma growth, metabolism, and antibody production. *Biotechnolo. Bioeng.* 37:989-993.

Sharfstein S, Shen D, Kiehl T R, Zhou R. (2007) Molecular response to osmotic shock. In: *Cellular Engineering: System Biology*, Volume 5. Edited by Mohamed A-R, Martin F. (Springer publisher).

Shen C F, Voyer R, Tom R, Kamen A. (2010) Reassessing culture media and critical metabolites that affect adenovirus production. *Biotechnol. Prog.* 26:200-207.

Sun Z, et al. (2004) Hyperosmotic stress in murine hybridoma cells: effects on antibody transcription, translation, posttranslation processing and the cell cycle. *Biotechnol. Prog.* 20:576-589.

Transfiguracion J, Bernie, A, Voyer R, Coelho H, Coffey M, Kamen A. (2008) Rapid and reliable quantification of reovirus type 3 by high performance liquid chromatography during manufacturing of Reolysin. *J Pharm Biomed Anal.* 48, 598-605.

Transfiguracion J, Mena J A, Aucoin M G, Kamen A A. (2011) Development and validation of a HPLC method for the quantification of baculovirus particles. *J Chromatogr B Analyt Technol Biomed Life Sci.* 879, 61-68.

Waite M R F, Pfefferkorn E R. (1970) Inhibition of sindbis virus production by media of low ionic strength: intracellular events and requirements for reversal. *J. Virol.* 5:60-71.

Xie, L., Goochee, C. F. (2008) Methods of adenovirus production, U.S. Pat. No. 7,344,873

Zhang C, Ferreira T B, Cruz P E, Alves P M, Haury M, Carrondo M J T. (2006) The importance of 293 cell cycle phase on adenovirus vector production. *Enzy. Microb. Technol.* 39:1328-1332.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

What is claimed is:

1. A method of using a mammalian cell to produce virus comprising:
A) growing mammalian cells under hyperosmotic conditions during a growth phase of the cells in a cell culture media;

B) diluting the cell culture media to achieve less stressful osmotic conditions by adding diluent directly to the cell culture media to lower the osmolality of said cell culture media;

C) following said diluting, infecting or transfecting the cells with a non-budding virus selected from the group consisting of an adenovirus and a reovirus to initiate a viral production phase by the cells; and, D) maintaining the infected or transfected cells under less stressful osmotic conditions during the viral production phase to produce more of the virus than that produced by cells grown under isotonic conditions.

2. The method according to claim 1, wherein the virus is a baculovirus.

3. The method according to claim 1, wherein the virus is a viral vector.

4. The method according to claim 1, wherein the hyperosmotic conditions comprise an osmolality of 330 mOsm or greater without inducing cell death.

5. The method according to claim 1, wherein the hyperosmotic conditions comprising an osmolality of 370 mOsm or greater without inducing cell death.

6. The method according to claim 1, wherein the hyperosmotic conditions comprise an osmolality in a range of from 330 mOsm to 420 mOsm.

7. The method according to claim 1, wherein the hyperosmotic conditions comprise an osmolality in a range of from 330 mOsm to 370 mOsm.

8. The method according to claim 1, wherein the mammalian cells comprise human embryonic kidney 293 cells, A549 cells, Chinese hamster ovary cells or Hela cells.

9. The method according to claim 1, wherein the hyperosmotic conditions comprise an osmolality in a range of from 370 mOsm to 420 mOsm.

10. The method according to claim 1, wherein the less stressful osmotic conditions during the production phase comprise an osmolality in a range of 250-325 mOsm.

11. The method according to claim 1, wherein the less stressful osmotic conditions during the production phase comprise an osmolality in a range of 280-300 mOsm.

12. The method according to claim 1, wherein the less stressful osmotic conditions during the production phase comprise an osmolality in a range of 285-295 mOsm.

13. The method according to claim 1, wherein the less stressful osmotic conditions during the production phase comprise an osmolality of about 290 mOsm.

14. A method of using an insect cell to produce virus comprising:

A) growing insect cells in a cell culture media under hyperosmotic conditions during a growth phase of the cells;

B) diluting the cell culture media to achieve less stressful osmotic conditions by adding diluent directly to the cell culture media to lower the osmolality of said cell culture media;

C) following said diluting, infecting or transfecting the cells with a non-budding virus selected from the group consisting of an adenovirus and a reovirus to initiate a viral production phase by the cells; and, D) maintaining the infected or transfected cells under less stressful osmotic conditions during the viral production phase to produce more of the virus than that produced by cells grown under isotonic conditions.

15. The method according to claim 14, wherein the insect cells comprise SF9 cells.

* * * * *